(12) United States Patent
Kandori (10) Patent No.: US 11,141,058 B2
(45) Date of Patent: Oct. 12, 2021

(54) DYNAMIC VISUAL ACUITY MEASURING DEVICE AND DYNAMIC VISUAL ACUITY MEASURING METHOD

(71) Applicant: MAXELL, LTD., Kyoto (JP)

(72) Inventor: Akihiko Kandori, Tokyo (JP)

(73) Assignee: MAXELL, LTD., Kyoto (JP)

( * ) Notice: Subject to any disclaimer, the term of this patent is extended or adjusted under 35 U.S.C. 154(b) by 233 days.

(21) Appl. No.: 16/470,134

(22) PCT Filed: Feb. 6, 2018

(86) PCT No.: PCT/JP2018/004010
§ 371 (c)(1),
(2) Date: Jun. 14, 2019

(87) PCT Pub. No.: WO2018/147277
PCT Pub. Date: Aug. 16, 2018

(65) Prior Publication Data
US 2020/0077884 A1     Mar. 12, 2020

(30) Foreign Application Priority Data
Feb. 10, 2017   (JP) .............................. JP2017-022999

(51) Int. Cl.
*A61B 3/032* (2006.01)
(52) U.S. Cl.
CPC .................................... *A61B 3/032* (2013.01)
(58) Field of Classification Search
CPC ...................................................... A61B 3/032
(Continued)

(56) References Cited

U.S. PATENT DOCUMENTS 6,062,692 A  *  5/2000  Ishigaki ................. A61B 3/028
                                                       351/243
8,303,120 B2 * 11/2012  Hoshino ................... H04N 5/74
                                                        353/79

FOREIGN PATENT DOCUMENTS

JP        H11164815 A     6/1999
JP        2004-4276 A     1/2004
(Continued)

OTHER PUBLICATIONS

International Search Report issued in corresponding International Patent Application No. PCT/JP2018/004010, dated Apr. 24, 2018.
(Continued)

*Primary Examiner* — Mohammed A Hasan
(74) *Attorney, Agent, or Firm* — McDermott Will & Emery LLP (57) ABSTRACT

Provided is a technique with which it is possible to measure a subject's reaction by moving a visual target object in an arbitrarily defined direction as well as a horizontal direction. A dynamic visual acuity measuring device includes a projector projecting an index image pattern, a reflecting mirror reflecting light from the projector, a screen receiving light from the reflecting mirror and displaying the index image pattern, a movable casing holding and maintaining relative positions of the projector, the reflecting mirror, and the screen, a fixed casing supporting the movable casing, and a rotating shaft linking the movable casing rotatably to the fixed casing. In this device, the index image pattern displayed on the screen is moved in one direction by the reflecting mirror being displaced and a direction of movement of the index image pattern is changed in a coordinate system fixed to the fixed casing by the rotating shaft being rotated.

15 Claims, 12 Drawing Sheets

(58) Field of Classification Search
USPC .......................................................... 351/237
See application file for complete search history.

(56) References Cited

FOREIGN PATENT DOCUMENTS

| | | |
|---|---|---|
| JP | 2005-253503 A | 9/2005 |
| JP | 2007-020919 A | 2/2007 |
| JP | 2009-92728 A | 4/2009 |
| JP | 2010-48897 A | 3/2010 |
| JP | 2013-500836 A | 1/2013 |
| KR | 10-2009-0110697 A | 10/2009 |
| WO | 2011/017331 A1 | 2/2011 |

OTHER PUBLICATIONS

Notice of Reasons for Refusal issued in corresponding Japanese Patent Application No. 2017-022999, dated Jan. 19, 2021, with English machine translation.
Chinese Office Action issued in corresponding Chinese Patent Application No. 201880004193.4, dated Mar. 10, 2021, with English machine translation.

\* cited by examiner

| PROGRAM No. | INDEX IMAGE PATTERN | CORRECT ANSWER |
|---|---|---|
| 1 | ◠ | UP |
| 2 | C | RIGHT |
| 3 | ◡ | DOWN |
| 4 | ⊃ | LEFT |

DYNAMIC VISUAL ACUITY MEASURING DEVICE AND DYNAMIC VISUAL ACUITY MEASURING METHOD

CROSS-REFERENCE TO RELATED APPLICATIONS

This application is the U.S. National Phase under 35 U.S.C. § 371 of International Application No. PCT/JP2018/004010, filed on Feb. 6, 2018, which claims the benefit of Japanese Application No. 2017-022999, filed on Feb. 10, 2017, the entire contents of each are hereby incorporated by reference.

TECHNICAL FIELD

The present invention relates to a technique for performing human eyesight-related measurement.

BACKGROUND ART

During a medical checkup and the like, measurement of eyesight for seeing a state where a target object is stationary (static visual acuity) is performed by, for example, a Landolt ring being seen. In addition, Patent Document 1 discloses measurement of eyesight for seeing a state where a target object is not stationary (dynamic visual acuity).

In Patent Document 1, a visual target image on a screen is moved in a predetermined direction for dynamic visual acuity measurement. Then, the speed of movement of the visual target image at the time of a subject's response to the moving visual target image is detected. The measurement is performed more than once, and the subject's dynamic visual acuity is measured on the basis of the average value of the speeds of movement.

CITATION LIST

Patent Document

Patent Document 1: JP 11-164815 A

SUMMARY OF THE INVENTION

Problems to be Solved by the Invention

It is said that visually obtained information accounts for 87% of all of the information that a person receives from the outside world through his or her sensory organs. Accordingly, examination of human reactions to various visually given stimuli is meaningful in examining people's physical or mental states.

In Patent Document 1, which proposes a method for dynamic visual acuity measurement, the visual target image on the screen moves only horizontally with respect to the subject. Accordingly, the human reaction that is obtained is limited to a reaction to a horizontally moving target.

The six muscles that move an eyeball are collectively referred to as the extraocular muscles. In most cases, motions changing the orientation of an eyeball are conducted on the basis of cooperation of the six muscles rather than the contraction of a single extraocular muscle. Extraocular muscle motions vary with the direction in which the eyeball is moved, and thus it is conceivable that the subject's reaction varies with the direction in which the visual target object moves. Accordingly, it is possible to obtain more information during human state examination once a subject's reaction is measured on the basis of visual target object movements in not only horizontal but also arbitrarily defined directions.

An object of the present invention is to provide a technique with which it is possible to measure a subject's reaction by moving a visual target object in an arbitrarily defined direction as well as a horizontal direction.

Solutions to Problems

An aspect of the present invention is a dynamic visual acuity measuring device including a projector projecting an index image pattern, a reflecting mirror reflecting light from the projector and including a displaceable reflecting surface, a screen receiving light from the reflecting mirror and displaying the index image pattern, a movable casing holding and maintaining relative positions of the projector, the reflecting mirror, and the screen, a fixed casing supporting the movable casing, and a rotating shaft linking the movable casing rotatably to the fixed casing.

Another aspect of the present invention is a dynamic visual acuity measuring method for reflecting light from a projector projecting an index image pattern by using a displaceable reflecting surface, projecting light from the reflecting surface onto a screen, moving the index image pattern on a screen as the reflecting surface is displaced, and presenting the index image pattern to a subject. A direction of movement of the index image pattern viewed from the subject is changed by relative positions of the projector, the reflecting surface, and the screen being maintained and the projector, the reflecting surface, and the screen being rotated about an axis of rotation.

Another aspect of the present invention is a dynamic visual acuity measuring device including a projector projecting an index image pattern, a reflecting mirror reflecting light from the projector, a screen receiving light from the reflecting mirror and displaying the index image pattern, a movable casing holding and maintaining relative positions of the projector, the reflecting mirror, and the screen, a fixed casing supporting the movable casing, and a rotating shaft linking the movable casing rotatably to the fixed casing. In this device, the index image pattern displayed on the screen is moved in one direction by the reflecting mirror being displaced and a direction of movement of the index image pattern is changed in a coordinate system fixed to the fixed casing by the rotating shaft being rotated.

Effects of the Invention

A technique can be provided with which it is possible to measure a subject's reaction by moving a visual target object in an arbitrarily defined direction as well as a horizontal direction.

MODE FOR CARRYING OUT THE INVENTION

An embodiment will be described in detail with reference to accompanying drawings. The present invention should not be construed as being limited to the following description of the embodiment. Those skilled in the art can easily understand that specific configurations of the present invention can be changed without departing from the spirit or gist of the present invention.

In the configuration of the invention described below, the same reference numerals are used for the same parts or parts having similar functions in different drawings so that the same description is omitted if necessary.

The position, size, shape, range, and the like of each configuration illustrated in the drawings and the like are to facilitate understanding of the invention, and thus may not be the actual position, size, shape, range, and the like. Accordingly, the present invention is not necessarily limited to the position, size, shape, range, and the like disclosed in the drawings and the like.

Figure 1:
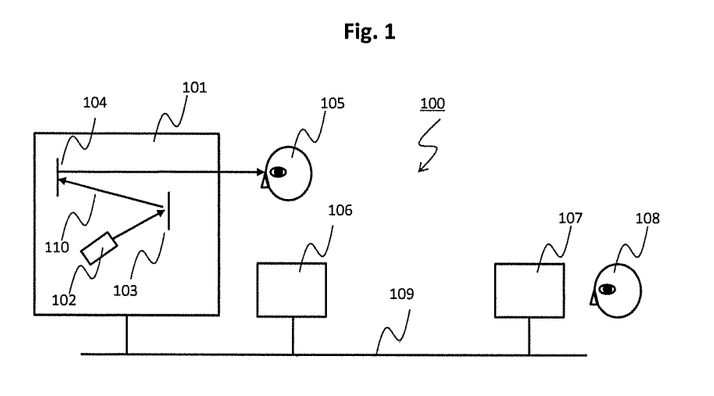
FIG. 1 is a block diagram illustrating the overall configuration of a dynamic visual acuity measuring device of an example.

FIG. 1 is a block diagram illustrating the overall configuration of a dynamic visual acuity measuring device of the present example. A dynamic visual acuity measuring device 100 includes a display device 101, an input device 106, and a control device 107.

The display device 101 includes a projector 102, a reflecting mirror 103, and a screen 104. A visual target image (visual target object) 110 projected from the projector 102 is reflected by the reflecting mirror 103 and projected onto the screen 104. An index image is configured to be capable of moving in one direction on the screen 104 by the reflecting mirror 103 being moved.

A subject 105 visually recognizes the index image displayed on the screen 104 and performs desired input to the input device 106 in accordance with the result of the visual recognition. The display device 101 and the input device 106 are controlled by the control device 107. The control device 107 is operated by an operator 108. The display device 101, the input device 106, and the control device 107 are capable of transmitting and receiving signals and data by means of a line 109. The line 109 may be a wired line or a wireless line.

Figure 2:
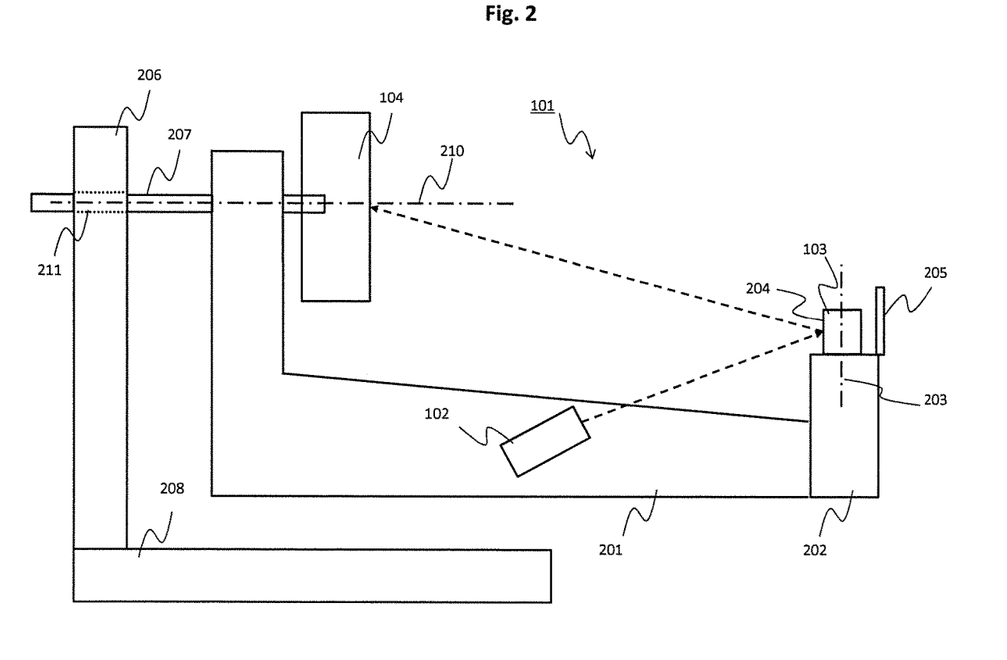
FIG. 2 is a side view illustrating a configuration example of a display device.

FIG. 2 is a side view illustrating an example of the display device 101. The display device 101 is capable of moving the visual target image in an arbitrarily defined direction when viewed from the subject 105. The configuration of the display device 101 will be described with reference to FIG. 2.

The display device 101 is provided with a movable casing 201 and a fixed casing 206. The projector 102 is incorporated in the movable casing 201. The projector 102 is, for example, a projector using a liquid crystal. A small projector having a size of approximately 10 to 20 cm square is already commercially available, and thus the projector can be used as the projector 102. The projector 102 projects the visual target image. The image data of the visual target image is transmitted from the control device 107 to the projector 102. As for the index image, the direction of a pattern can be visually recognized when, for example, the image is stationary. Although Landolt rings are representative, the index image does not have to be limited to the rings. In addition, the index image may be one in which a difference in type or size can be distinguished instead of the direction. For example, the index image is a pattern such as alphabet and hiragana.

The projector 102 projects the index image onto the reflecting mirror 103. The reflecting mirror 103 can be rotated about a mirror rotating shaft 203 by a motor 202. The angle of a reflecting surface 204 changes as a result, and thus the index image reflected by the reflecting surface 204 and projected on the screen 104 moves in, for example, a direction perpendicular to the page. A plane mirror may be used as the reflecting mirror. Alternatively, a curved mirror may be used as the reflecting mirror. Regarding the configurations of the reflecting mirror 103 and the screen 104 not specifically described in this specification, Patent Document 1 or the like may be followed.

With the above configuration, the subject 105 observing the screen 104 from the right-hand direction of FIG. 2 observes the index image moving in, for example, the direction perpendicular to the page. A shielding portion 205 is on the subject side of the reflecting mirror 103 such that the light from the projector 102 does not directly hit the subject.

Adopted in the present example is a configuration in which the index image is moved in the arbitrarily defined direction as well as the direction perpendicular to the page. Accordingly, the movable casing 201 is configured to be rotatable about a rotating shaft 207 with respect to the fixed casing 206. In other words, the rotating shaft 207 fixed to, for example, the movable casing 201 is rotatably held in a through hole 211 provided in the fixed casing 206. Once the rotating shaft 207 rotates, the movable casing 201 and the projector 102, the reflecting mirror 103, and the screen 104 held by the movable casing 201 rotate together around a central axis 210. As a result, the direction of movement of the index image projected onto the screen 104 changes as a result of the rotation. The direction of the rotating shaft 207 is set to be substantially the same as the subject's gaze direction. Although not illustrated in FIG. 2, a jaw fixing base is also disposed near the shielding portion 205 such that an eye of the subject 105 is placed on the central axis 210 and the eye of the subject 105 comes to a position on the mirror rotating shaft 203 (and the distance between the eye of the subject 105 and the screen 104 is kept constant).

The fixed casing 206 is fixed to an installation portion 208. The installation portion 208 holds the entire display device 101. Since a small liquid crystal projector is used as the projector 102, the display device 101 in FIG. 2 is portable in size. The display device 101 can be used with the installation portion 208 appropriately placed on an installation surface on a desk, a floor, and the like.

Figure 3:
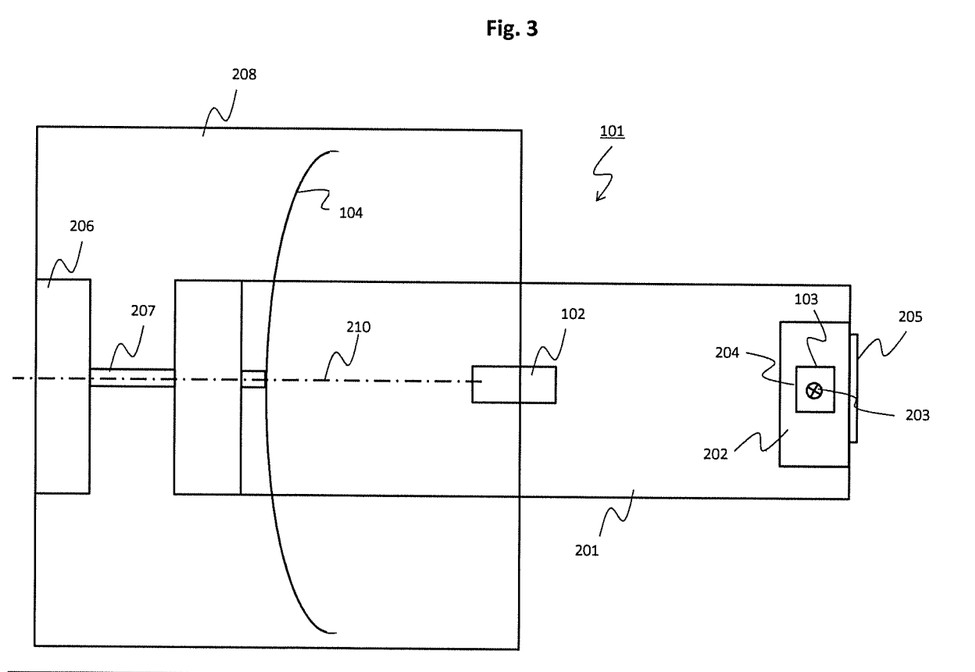
FIG. 3 is a top view illustrating the configuration example of the display device.

FIG. 3 is a top view of the display device 101 in FIG. 2. The screen 104 has, for example, a rectangular shape and has a flat surface or a curved surface (usually, a semicircular shape about the axis of rotation of the reflecting surface 204). It is preferable to move the index image in the long side direction of the rectangular shape (upward-downward direction of the page in FIG. 3). Although the projector 102 is disposed in front of the screen 104 in the example that is illustrated in FIG. 3, the disposition of the projector 102 can be freely changed by means of another reflecting mirror installed between the projector 102 and the reflecting mirror 103 and a bent optical axis.

Figure 4:
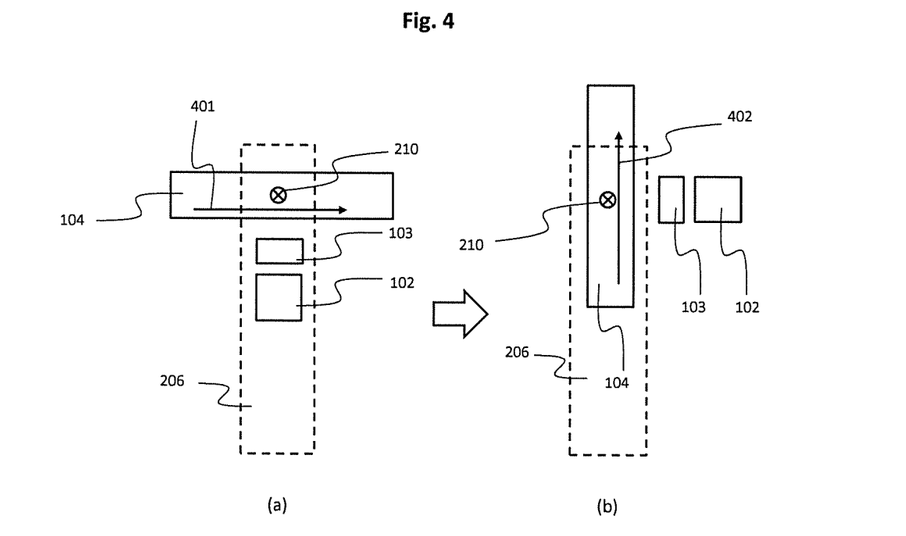
FIG. 4 is a schematic diagram in which the display device is viewed from a subject side.

FIG. 4 is a schematic diagram in which the display device 101 is viewed from the subject 105 side. Illustrated in FIG. 4 is the direction of movement of the index image resulting from the rotation of the movable casing 201. The state that is illustrated in FIG. 4(a) illustrates the state that is illustrated in FIGS. 2 and 3, and the index image moves from the left to the right in the horizontal direction of the page as indicated by an arrow 401. Illustrated in FIG. 4(b) is a state where the movable casing 201 has rotated by 90 degrees about the central axis 210 and to the left (counterclockwise) as viewed from the subject 105 from the state illustrated in FIG. 4(a). As the movable casing 201 rotates, the projector 102, the reflecting mirror 103, and the screen 104, which are configured integrally with the movable casing, rotate about the rotating shaft 207. Accordingly, the index image moves upward from below in the vertical direction of the page as indicated by an arrow 402.

Meanwhile, the position of the fixed casing 206, which is indicated by a dotted line, remains unchanged. Accordingly, in another expression, rotating shaft rotation results in a change in the direction of index image pattern movement in the coordinate system that is fixed to the fixed casing (this is equivalent to the coordinate system that is recognized by the subject).

The rotating shaft 207 may be mechanically fixed to the fixed casing 206 with a screw or the like. In a case where the movable casing 201 is rotated, the screw is loosened and the movable casing 201 is manually rotated about the central axis 210. Once the position is fixed, the movable casing 201 is fixed by the screw being tightened. Alternatively, the rotating shaft 207 may be rotated by means of a motor or the like.

Figure 5:
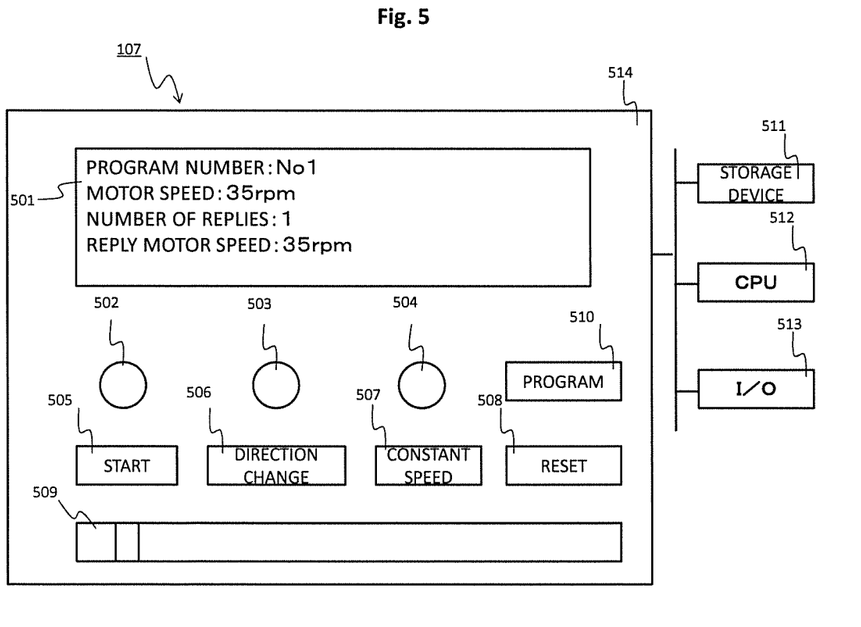
FIG. 5 is a block diagram illustrating a configuration example of a control device.

FIG. 5 is a block diagram illustrating a block configuration and an operation screen example of the control device 107. In the present example, the control device 107 is controlled by software and by means of a small information processing device such as a personal computer. The information processing device is provided with a storage device 511, a central processing unit (CPU) 512, and an input interface and an output interface (collectively referred to as "input-output interface 513"). As for functions such as calculation and control in the present example, the display device 101 or the input device 106 is caused to perform predetermined processing by means of the input interface or the output interface and by the program that is stored in the storage device 511 being executed by the CPU 512. Alternatively, similar control can be configured with hardware alone without software being used.

A layout 514 illustrated in FIG. 5 is a screen for control that is displayed on the monitor screen of the control device 107. Here, it is assumed that input is performed on the control device 107 by a monitor having a touch panel function. In the case of hardware-only configuration using no software, a mechanical push button switch or the like may be used.

A display window 501 displays various types of information necessary for operation. Examples of the information include a program number, the current speed of the motor 202, the number of replies from the subject 105, and the speed of the motor at a reply timing. The motor speed may be display after conversion into, for example, the speed of movement of the index image on the screen.

A start display 502 is turned on while the motor 202 rotates and turned off while the motor 202 is in a stop state.

A direction display 503 indicates the direction of rotation of the motor 202. For example, the direction display 503 is turned on while the motor 202 rotates in the clockwise direction and turned off while the motor 202 rotates in the counterclockwise direction.

A constant speed display 504 is turned on while the motor rotates at a constant speed.

The motor 202 starts to rotate when a start switch 505 is pressed. The motor 202 stops once the start switch 505 is pressed again.

The motor 202 rotates in the clockwise direction once a direction change switch 506 is pressed. The motor 202 rotates in the counterclockwise direction once the direction change switch 506 is pressed again.

The motor 202 rotates at a constant speed once a constant speed switch 507 is pressed.

A reset switch 508 is pressed at the end of inspection or before inspection initiation. Then, the display window 501 and the motor 202 return to the initial state.

The rotation speed of the motor 202 can be changed by a speed adjustment lever 509 being slid.

A program number can be input to a program number input window 510. It is possible to select a pattern of inspection in accordance with the number by inputting the program number. The inspection pattern includes an index image type. A pattern of change in motor rotation speed and the like can be included as well.

Figure 6:
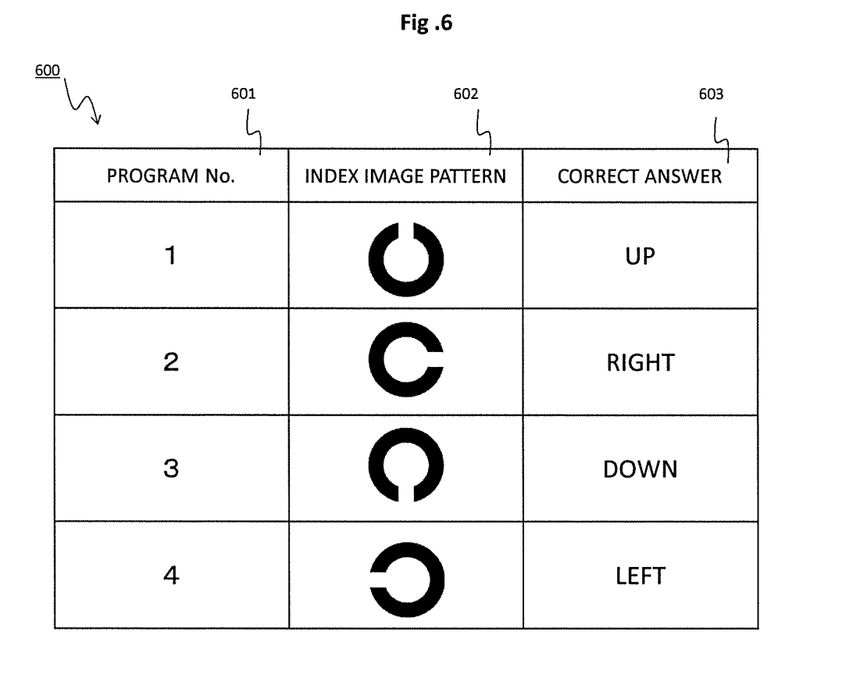
FIG. 6 is a table diagram illustrating an example of a correspondence table of a program number, an index image pattern corresponding to the program number, and a correct answer.

FIG. 6 is a table diagram illustrating an example of a correspondence table 600 of a program number 601, an index image pattern 602 corresponding to the program number 601, and a correct answer 603 with respect to the reply of the subject 105. Once the program number 601 is input or selected on the program number input window 510, the index image pattern 602 is sent to the projector 102 and the index image pattern 602 is displayed on the screen 104. Upon seeing the displayed index image pattern 602, the subject 105 inputs the orientation of the displayed index image pattern 602 as a reply to the input device 106. The reply is sent to the control device 107 and collated with the correct answer 603. The data of the correspondence table 600 is prepared in advance by the operator 108 or the like and stored in the storage device 511 of the control device 107. When the display is performed, image data is transmitted from the input-output interface 513 to the projector 102 of the display device 101.

The subject 105 is supposed to input the direction of the very index image pattern 602 that he or she sees to the input device 106. In the present example, the optical system that reaches the screen 104 from the projector 102 rotates as a single unit. Accordingly, even if the same index image pattern 602 is displayed, the orientation of the index image pattern 602 viewed from the subject 105 appears different depending on the rotation angle of the movable casing 201. Accordingly, it is necessary to define the state of the screen 104 that is presumed by the correct answer 603 with respect to the reply of the subject 105 or the index image pattern 602. In the present example, the index image pattern 602 and the correct answer 603 in FIG. 6 pertain to a case where the screen 104 has an angle of zero degrees. Here, the zero angle of the screen 104 is defined to refer to the state that is illustrated in FIG. 4(a). In this case, the angle of the screen 104 is −90 degrees in the state that is illustrated in FIG. 4(b).

Figure 7:
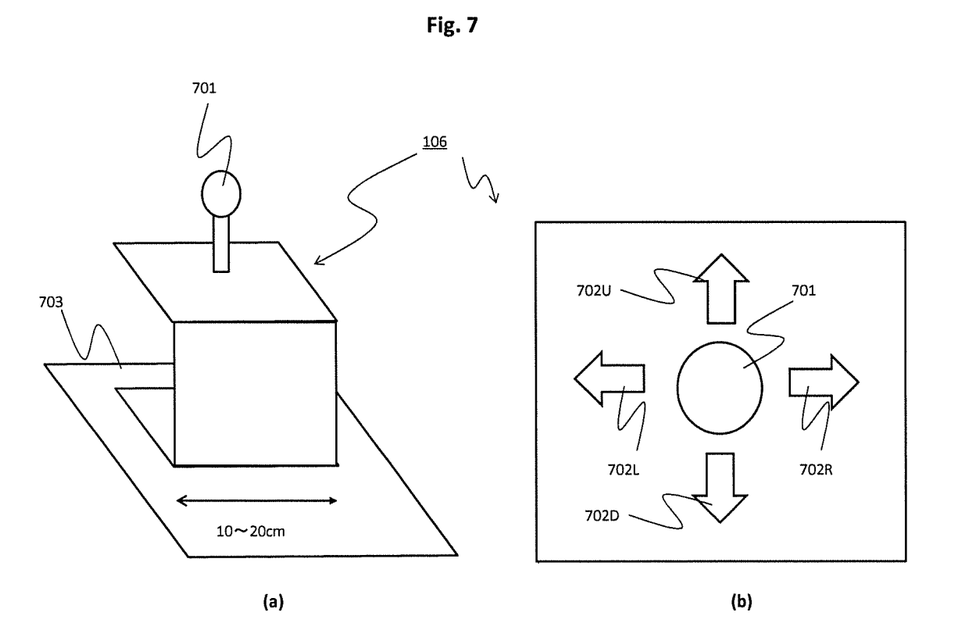
FIG. 7 is a perspective view and an enlarged top view of an input device.

Illustrated in FIG. 7 is an example of the input device 106 operated by the subject 105, in which FIG. 7(a) is a perspective view and FIG. 7(b) is an enlarged top view. A joystick enabling input in four directions or the like can be used as the input device 106. The directions in which the input can be performed may be more than four directions or less than four directions in accordance with the index image pattern 602. As illustrated in FIG. 7(a), the input device 106 has an independent casing and is movably installed on a pedestal surface 703 installed in front of the subject 105. Illustrated in FIG. 7(b) is the upper surface of the device that is viewed from the subject 105 in a state where the subject 105 has installed the input device 106 on the pedestal in front of himself or herself. As illustrated in FIG. 7(b), arrows 702U, 702D, 702L, and 702R corresponding to upward, downward, leftward, and rightward input directions are displayed on the input device.

The subject 105 operates a lever 701 in accordance with the index image pattern 602 on the screen 104 that he or she sees. For example, the subject 105 operates the lever 701 in the direction that is indicated by the upward arrow 702U in a case where the subject 105 recognizes that a Landolt ring with an upper gap is seen on the screen 104. The input device outputs a signal indicating "up" when the lever 701 is operated in the upward arrow 702U direction.

The signal corresponding to the operation of the lever 701 is sent to the control device 107 and collated with the correct answer 603. In the case of FIG. 6, the Landolt ring with the upper gap is the index image pattern of program No1. Accordingly, in a case where measurement is performed on the basis of program No1, the signal indicating "up" is the correct answer. In a case where measurement is performed on the basis of programs No2 to 4, the signal indicating "up" is an incorrect answer. The motor rotates until the subject-collated result is "correct answer". There are two measurement modes at this time. One is a measurement mode in which the rotation speed of the motor 202 is measured with a delay for each point from the set speed of a normal method. The other is a measurement mode in which measurement is performed while the motor 202 rotates at a constant rotation speed at all times in a constant speed mode.

Although a mechanical joystick is used as the input device 106 in the above example, a touch panel-type input device may be used instead. In the present example, the input device 106 is, for example, approximately 10 to 20 cm square in size and configured as an independent casing separate from the control device 107 and the display device 101. The input device 106 facilitates a change in orientation.

As described in the above example, in the present example, the orientation of the optical system is rotatable, and thus the orientation of the index image pattern 602 on the screen 104 viewed from the subject 105 varies with the rotation angle of the optical system. Accordingly, once the input device 106 is operated in accordance with the orientation of the very index image pattern 602 that the subject 105 sees, it is impossible to correspond to the correct answer determined correspondingly to the index image pattern 602 as illustrated in FIG. 6.

Figure 8:
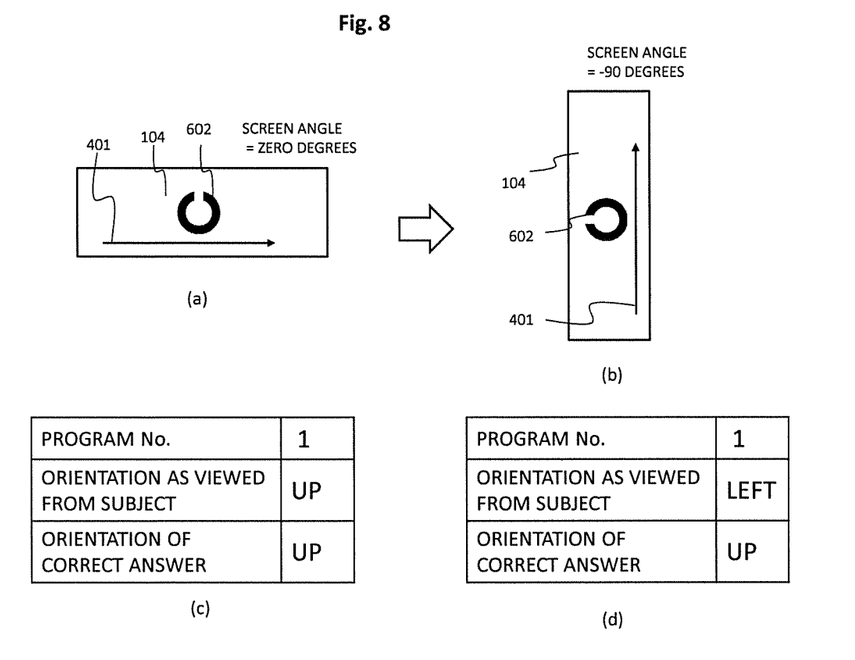
FIG. 8 is a conceptual diagram illustrating a relationship of the index image pattern displayed on a screen, the orientation in which a subject sees the index image pattern, and the orientation of the correct answer.

This problem will be described with reference to FIG. 8. Illustrated in the upper half of FIG. 8 is the index image pattern 602 displayed on the screen 104 correspondingly to the states of FIGS. 4(a) and 4(b). In other words, FIG. 8(a) illustrates the case of a screen angle of zero degrees and FIG. 8(b) illustrates the case of a screen angle of −90 degrees. Here, it is assumed that the index image pattern of program No1 in FIG. 6 is displayed. As described in the description of FIG. 6, the correspondence table in FIG. 6 is on the premise that the screen angle is zero degrees. As illustrated in FIG. 8(a), the index image pattern of program No1 is upward at the screen angle of zero degrees. At the screen angle of −90 degrees, however, the index image pattern is displayed with a leftward orientation as illustrated in FIG. 8(b).

Considered here is a case where the subject 105 performs input to the input device 106 installed as illustrated in FIG. 7(b). The correct answer 603 with respect to the index image pattern 602 pertains to a case where the angle of the screen 104 is zero degrees. In a case where the screen 104 has an angle of zero degrees, the subject operates the lever of the input device in FIG. 7(b) in the direction of 702U as illustrated in FIG. 8(c) in a case where the subject 105 correctly recognizes the index image pattern. At this time, the orientation input by the subject matches the orientation of the correct answer.

In a case where the angle of the screen 104 is −90 degrees, the subject operates the lever of the input device in FIG. 7(b) in the direction of 702L as illustrated in FIG. 8(d) even in a case where the subject correctly recognizes the index image pattern. As a result, the orientation input by the subject does not match the orientation of the correct answer.

Figure 9:
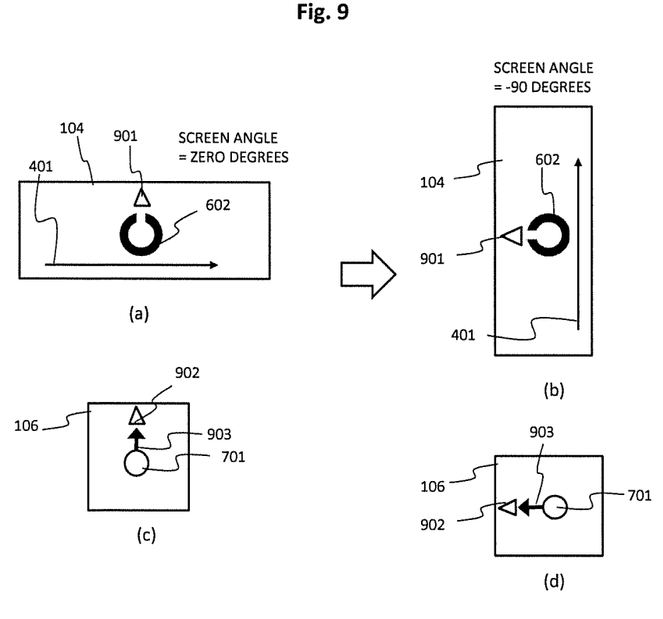
FIG. 9 is a conceptual diagram illustrating a relationship of the index image pattern displayed on the screen and the orientation of the input device.

Illustrated in FIG. 9 is a configuration for addressing this problem with ease. A direction-indicating first mark 901 is added to the screen 104. A direction-indicating second mark 902 is added to the input device 106. The marks may be marks printed on the screen 104 and the input device 106. Alternatively, adhesion or the like may be performed with another member. The surface on which the index image pattern 602 is displayed is easy to see as a position to which the first mark 901 is added. The surface on which input means such as the lever 701 of the input device 106 is disposed is easy to see as a position to which the second mark 902 is added.

When the subject 105 operates the input device 106, the input device 106 is used after the direction of the second mark of the input device 106 is aligned with the direction that corresponds to the first mark 901 of the screen 104. As a simple method, marks with which directions can be grasped with ease, such as a triangle and an arrow, are used as the first and second marks and the input device 106 is set, such that the first and second marks coincide in direction with each other, before the input device 106 is operated.

In a case where the screen angle is zero degrees, for example, the input device 106 is installed such that the second mark 902 faces upward as viewed from the subject as illustrated in FIG. 9(c). In a case where the screen angle is −90 degrees, the input device 106 is installed such that the second mark 902 faces leftward as illustrated in FIG. 9(d). In this manner, an input direction 903 is the same as in a case where the screen angle is zero degrees in the coordinates fixed to the input device 106 even in the event of leftward input in accordance with the index image pattern 602 recognized by the subject 105 in the case of the screen angle of −90 degrees. Accordingly, the same input signal as in the case of FIG. 9(c) is obtained from the input device 106, and thus it is possible to correct the correspondence between the subject's input and the correct answer on the basis of the correspondence table 600 in FIG. 6.

According to the present example, it is possible to obtain a correct test result, even without any other signal processing and regardless of the orientation of the screen 104, simply by adding the marks to the screen 104 and the input device 106 and adopting the orientation-changeable configuration for the input device 106.

Figure 10:
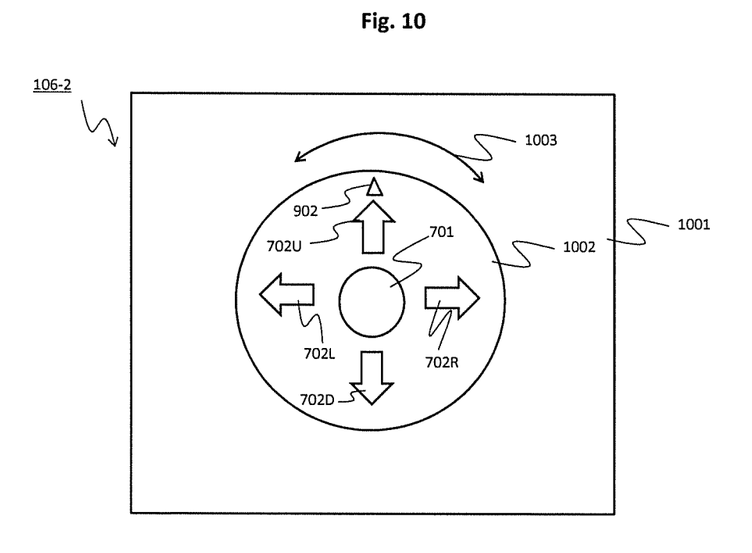
FIG. 10 is a top view illustrating another example of the input device.

FIG. 10 is a top view illustrating another configuration example of the input device 106. An input device 106-2 is provided with a fixed casing 1001 and an input portion 1002 rotatable with respect to the casing 1001. The input portion 1002 is capable of rotating in the direction of an arrow 1003 and is capable of matching the second mark 902 to the first mark 901 on the screen. In a case where the movable casing 201 of the display device 101 is rotated by means of a motor or the like in this configuration, the input portion 1002 may be rotated by means of a motor or the like in conjunction with the movement.

In the configuration described above, the orientation of the input device 106 is mechanically aligned with the screen 104. The mechanical alignment can be replaced with signal processing.

Figure 11:
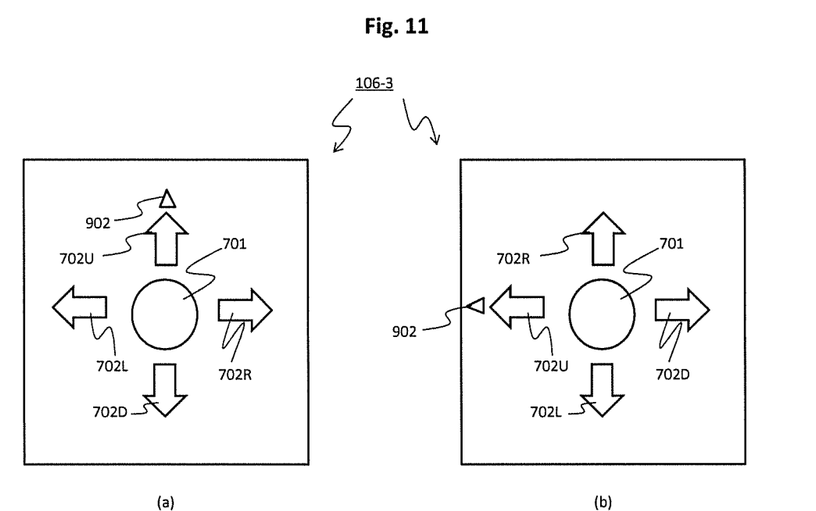
FIG. 11 is a top view illustrating yet another example of the input device.

FIG. 11 is a top view illustrating another configuration example of the input device 106. This input device is configured such that an input direction-indicating arrow is displayed on a liquid crystal screen of a portable terminal or the like and directional input is performed by the subject 105 being caused to touch the arrow by means of a touch panel mechanism. FIG. 11(a) pertains to a case where the screen angle is zero degrees. The second mark 902 is displayed upward on the liquid crystal screen, the arrows 702U, 702D, 702L, and 702R are displayed as input directions, and signals corresponding to the input directions are output. FIG. 11(b) pertains to a case where the screen angle is −90 degrees. The second mark 902 is displayed leftward and the arrows 702U, 702D, 702L, and 702R are displayed as input directions. The output signals are shifted counterclockwise with respect to the arrows whereas the arrows displayed on the input device 106 are identical to those illustrated in FIG. 11(a). As a result, the correspondence between the subject's input and the correct answer can be corrected on the basis of the correspondence table 600 in FIG. 6, similarly to the examples illustrated in FIGS. 9 and 10, even if the subject 105 inputs the very index image pattern that he or she sees.

The input device of the present example is configured such that the correspondence relationship between the input operation that the subject performs in order to perform input and the signal output as a result of the input can be changed on the basis of the rotation angles of the movable casing and the fixed casing. Such a configuration can be performed simply by display screen and output signal switching and can be realized with a simple program or hardware. The example that is illustrated in FIG. 11 is excellent in durability because the device is free from a burden attributable to a mechanical movement and a signal processing-based response is possible. In addition, the input device can be set without manual intervention. Accordingly, the first mark 901 and the second mark 912 may be omitted in this case.

An example of a measurement procedure using the dynamic visual acuity measuring device 100 described above will be described with reference to FIG. 12. Prior to the start, the subject 105 stands by at a position where the screen 104 is visible and the input device 106 can be operated. The operator 108 sets the angle of the screen 104 of the display device 101 (processing S1201). Next, the operator 108 or the subject 105 who received guidance sets the orientation of the input device 106 on the basis of the direction indicated by the first mark 901 of the screen 104 in, for example, the manner that is illustrated in FIG. 9 (processing S1202). The setting at this time is facilitated by the second mark of the input device 106 being referred to.

Figure 12:
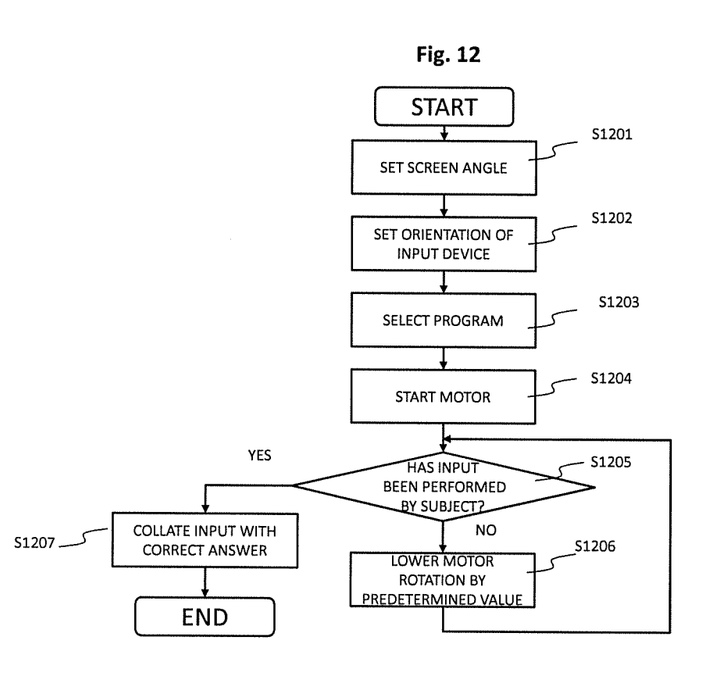
FIG. 12 is a flow diagram illustrating a procedure for operating the dynamic visual acuity measuring device of the example.

The operator 108 operates the control device 107 and selects a program (processing S1203). Subsequently, the operator 108 rotates the motor 202 (processing S1204). The motor 202 is rotated at any speed and in any direction. The index image pattern projected on the screen 104 moves as the motor 202 rotates.

The subject 105 gazes the index image pattern projected on the screen 104. In a case where the pattern is recognizable and the index image pattern is a Landolt ring, for example, the subject 105 inputs the cut orientation of the ring from the input device 106 (processing S1205). In a case where nothing is input, the speed of movement of the index image pattern is reduced by the rotation speed of the motor 202 being lowered (processing S1206). The rotation speed of the motor 202 may be manually controlled by the operator 108 or may be automatically controlled by the control device 107. In a case where input is performed, collation is performed with the correct answer for each program as illustrated in FIG. 6 (processing S1207). Normally, a measurement result is obtained on the basis of the speed of movement at the timing of the correct answer. In the above description, the measurement is performed in the direction of motor rotation speed reduction. Alternatively, the measurement can be performed in the opposite direction or at a constant speed.

The present invention is not limited to the embodiment described above. The present invention includes various modification examples. For example, a part of the configuration of one example can be replaced with the configuration of another example and the configuration of another example can be added to the configuration of one example. In addition, the configuration of another example can be added, deleted, or replaced with respect to a part of the configuration of each example.

INDUSTRIAL APPLICABILITY

The present invention can be used for a technique for performing human eyesight-related measurement.

REFERENCE SIGNS LIST

100 Dynamic visual acuity measuring device
101 Display device
102 Projector
103 Reflecting mirror
104 Screen
105 Subject
106 Input device
107 Control device
108 Operator

The invention claimed is:
1. A dynamic visual acuity measuring device comprising:
a projector projecting an index image pattern;
a reflecting mirror reflecting light from the projector and including a displaceable reflecting surface;
a screen receiving light from the reflecting mirror and displaying the index image pattern;
a movable casing holding and maintaining relative positions of the projector, the reflecting mirror, and the screen;
a fixed casing supporting the movable casing; and
a rotating shaft linking the movable casing rotatably to the fixed casing.
2. The dynamic visual acuity measuring device according to claim 1, comprising:

an input device for receiving input from a subject visually recognizing the index image pattern displayed on the screen; and a control device storing correct answer information associated with the type of the index image pattern.

3. The dynamic visual acuity measuring device according to claim 2, wherein the screen is provided with a direction-indicating first mark, and the input device is provided with a direction-indicating second mark.

4. The dynamic visual acuity measuring device according to claim 3, wherein the first mark is disposed on a surface of the screen where the index image pattern is projected.

5. The dynamic visual acuity measuring device according to claim 3, comprising:

a display device including the movable casing, the fixed casing, and the rotating shaft; and a control device controlling the input device and the display device, wherein an independent casing separate from the control device and the display device constitutes the input device.

6. The dynamic visual acuity measuring device according to claim 3, wherein an input portion and an input device casing capable of performing relative rotation constitute the input device.

7. The dynamic visual acuity measuring device according to claim 2, wherein the input device is configured to be capable of changing a correspondence relationship between input operation for the input performed by a subject and a signal output as a result of the input.

8. The dynamic visual acuity measuring device according to claim 7, wherein the input device is configured to be capable of changing a correspondence relationship between input operation for the input performed by a subject and a signal output as a result of the input based on a rotation angle of the fixed casing with respect to the movable casing.

9. The dynamic visual acuity measuring device according to claim 1, wherein the rotating shaft is horizontal to a surface on which the fixed casing is installed.

10. The dynamic visual acuity measuring device according to claim 1, wherein the index image pattern is a Landolt ring.

11. A dynamic visual acuity measuring method for reflecting light from a projector projecting an index image pattern by using a displaceable reflecting surface, projecting light from the reflecting surface onto a screen, moving the index image pattern on a screen as the reflecting surface is displaced, and presenting the index image pattern to a subject, wherein a direction of movement of the index image pattern viewed from the subject is changed by relative positions of the projector, the reflecting surface, and the screen being maintained and the projector, the reflecting surface, and the screen being rotated about an axis of rotation.

12. The dynamic visual acuity measuring method according to claim 11, wherein the axis of rotation is substantially the same as a gaze direction of the subject.

13. The dynamic visual acuity measuring method according to claim 11, wherein the index image pattern has a pattern direction visually recognizable at least when the index image pattern is stationary.

14. The dynamic visual acuity measuring method according to claim 13, wherein a direction in which an input device is disposed is set, based on a first mark attached to the screen and a second mark attached to the input device, before input is received from a subject visually recognizing a direction of the index image pattern displayed on the screen and by the input device being used.

15. A dynamic visual acuity measuring device comprising:

a projector projecting an index image pattern;

a reflecting mirror reflecting light from the projector;

a screen receiving light from the reflecting mirror and displaying the index image pattern;

a movable casing holding and maintaining relative positions of the projector, the reflecting mirror, and the screen;

a fixed casing supporting the movable casing; and a rotating shaft linking the movable casing rotatably to the fixed casing, wherein the index image pattern displayed on the screen is moved in one direction by the reflecting mirror being displaced, and a direction of movement of the index image pattern is changed in a coordinate system fixed to the fixed casing by the rotating shaft being rotated.

* * * * *